United States Patent [19]

Williams

[11] 4,112,944

[45] Sep. 12, 1978

[54] TUBE CLAMP AND PIERCING DEVICE

[76] Inventor: Gayland M. Williams, 3 Maple St., North Springfield, Vt. 05150

[21] Appl. No.: 750,338

[22] Filed: Dec. 13, 1976

[51] Int. Cl.² .................................................. A61M 5/00
[52] U.S. Cl. ................................. 128/214 R; 128/346; 137/318; 222/83
[58] Field of Search ............ 128/214 R, 214 D, 214.2, 128/348, 346, 347; 137/318; 285/197; 222/83

[56] References Cited

U.S. PATENT DOCUMENTS

| | | | |
|---|---|---|---|
| 2,955,595 | 10/1960 | Semple | 128/214 D |
| 3,019,790 | 2/1962 | Militana | 128/322 |
| 3,252,475 | 5/1966 | Jones | 137/318 |
| 3,698,419 | 10/1972 | Tura | 137/318 |
| 3,981,322 | 9/1976 | Gebelius | 137/318 |
| 4,043,333 | 8/1977 | Munch | 128/214 R |

Primary Examiner—Dalton L. Truluck

Attorney, Agent, or Firm—Sughrue, Rothwell, Mion, Zinn and Macpeak

[57] ABSTRACT

A device for clamping a tubular conduct and piercing the wall of the conduct to establish fluid communication with the inside of the conduit includes a clamp having a pair of jaws which are openable to allow the clamp to be inserted around the conduit and closed to create a cradle for the conduit and allow the conduit to be pierced by a hollow piercing member carried by one clamp jaw. The jaws are readily and easily locked into position by locking tabs on one end of the jaws and the jaws are hinged together at the other end. Two embodiments are disclosed; one in which the device is used for medical purposes for tapping into a tube, e.g., as used for intravenous feeding, and the other for industrial purposes, e.g., for tapping into a tube transporting maple sucrose.

10 Claims, 9 Drawing Figures

TUBE CLAMP AND PIERCING DEVICE

BACKGROUND OF THE INVENTION

1. Field of the Invention

This invention relates to a clamp and piercing device to allow piercing of a tubular conduit.

2. Prior Art

It is known in the prior art to tap into tubular conduits by clamping the conduit and piercing the wall thereof. However, such devices as are known are cumbersome to operate and are not easily attached and detached from the conduit. Moreover, the piercing means have in the past cut the conduit to leave a plug which then is loose in the fluid which could cause contamination particularly if the device is used for medical purposes. This device overcomes the disadvantages in the known prior art of piercing tubular conduits by providing simple and relatively inexpensive device which can be easily applied or removed by simple finger action and when clamped stays clamp-tight while not allowing leakage nor relative movement nor plug cutting from the conduit wall.

SUMMARY OF THE INVENTION

This invention is illustrated in two embodiments, one for piercing lines such as used in hospitals for injecting fluid into the human body and the other in industrial applications such as piercing lines carrying maple sucrose or the like. In both embodiments, the basic principles are the same, namely, the clamp has a pair of clamping jaws which are hinged at one end and have locking tabs at the other end. Intermediate the ends of the jaws there are semi-circular depressions forming a cradle for tubular member to be pierced and one of the jaws carries the means for piercing such as a hollow needle. The jaws are readily opened and closed about the hinge and locked by the locking tabs. Because at least one of the the locking tabs is flexible and integral with the end of the jaws, the lock may be finger operated to allow ready opening and closing of the clamp. Appropriate seals are provided as necessary to prevent leaking of the fluid and the parts are configured to prevent relative movement of the clamped tube and the clamping and piercing device.

DETAILED DESCRIPTION OF THE PREFERRED EMBODIMENTS

Figure 1:
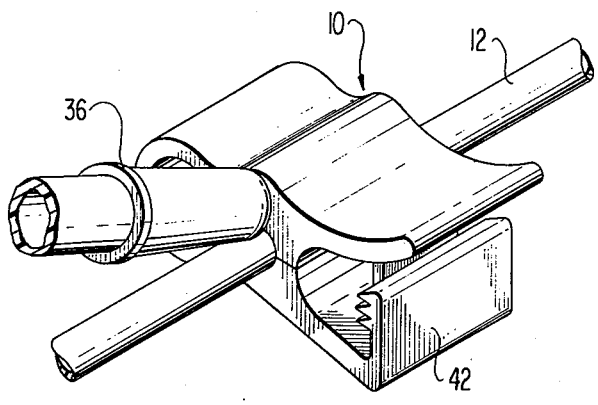
FIG. 1 is a perspective view of one embodiment of the clamping and piercing device of this invention as applied to medical and hospital technology.

A clamp and piercing device 10 for use in hospital applications, e.g. for piercing a tubular member 12 for insertion of fluids into a human body, is shown to be conveniently molded to provide two clamp jaws 14 and 16. The clamp jaws are connected by a hinge means 18 which in this embodiment is an integral hinge formed by molding a circular opening 20, the wall 22 of which forms the hinge. In addition the jaws 14 and 16 each have a semi-circular depression 24 and 26 respectively to accommodate and seat the tubular member 12. On each side of the semi-circular depressions there are flat lands 28 to control the size of the opening in the closed clamp made by the semi-circular depressions for accommodating the outside diameter of the tubular member 12.

Figure 4:
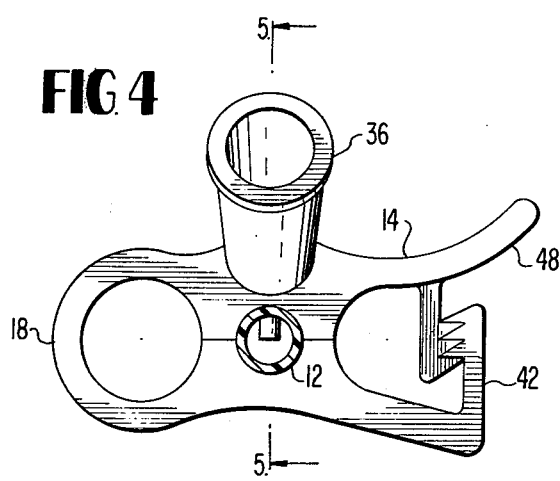
FIG. 4 is an end elevation view of the clamp in FIG. 1 with the clamp closed and the tube pierced.
Figure 5:
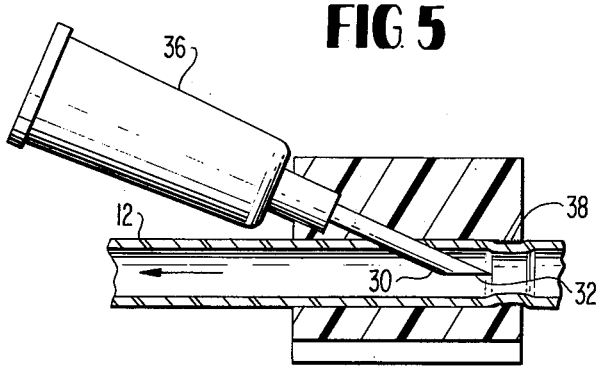
FIG. 5 is a section elevation view taken along lines 5—5 of FIG. 4.
Figure 6:
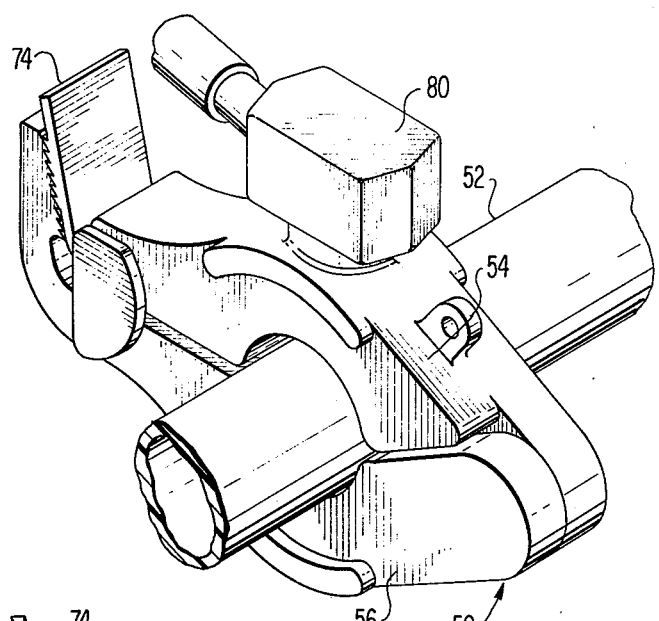
FIG. 6 is a perspective view of another embodiment of this invention as applied to industrial use, e.g., piercing maple sucrose arteries.

For piercing the tubular member 12, there is a hollowing piercing member 30 which in the embodiment shown can be a relatively conventional medical needle. The end 32 of the needle is as shown in FIGS. 4 and 5 parallel with the axis of the tubular member 12 when the clamp is closed. The needle 30 extends through body portion 34 of the clamp and has a hollow outer portion 36 to allow material to be injected into it and thence into tube 12. Molded into or inserted into the semi-circular depressions 24 and 26 is a friction means 38 which when the clamp is closed on the tubular member as shown in FIG. 5, further grips the tubular member and further assists in preventing any relative axial movement between the tubular member 12 and the needle 30.

Figure 2:
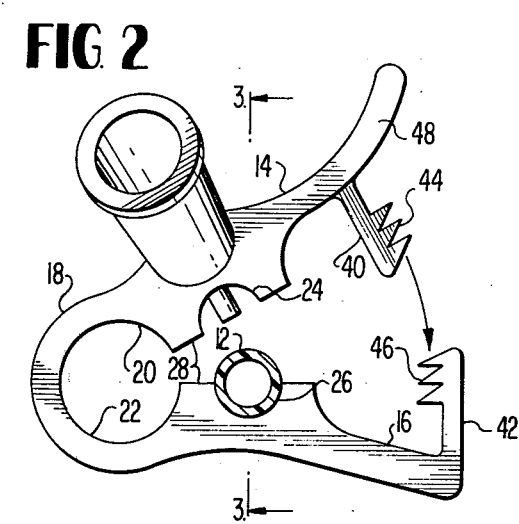
FIG. 2 is an end elevation of the device as shown in FIG. 1 with the clamp opened.
Figure 3:
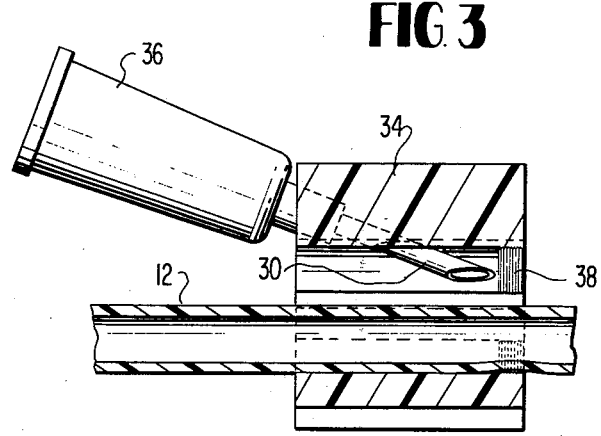
FIG. 3 is a sectional view taken along line 3—3 of FIG. 2.

The jaws 14 and 16 are normally open a shown in FIG. 2 to allow the clamp to be inserted on the tubular member 12. They carry a pair of locking tabs 40 and 42 and the locking tabs have complementary rachet teeth 44 and 46. The locking tabs are integrally molded to the ends of jaws 14 and 16 as shown in FIGS. 2 and 4 so that they are flexible. Jaw 14 has a further extension 48 for easy hand manipulation of the locking tab 44.

After the device has been inserted on a tubular member 12 as shown in FIG. 2, the clamping jaws are brought together and the complementary locking teeth 44 and 46 lock together. Then tubular member 12 is legally pulled in the direction of the arrow in FIG. 5 causing the needle 30 to pierce the wall of the tubular members. The interaction of the needle 30 and pulled tubular member 12 also provides a position stop for movement of the tubular member in the direction of the arrow and a controlled depth for the needle tip 32 which avoids piercing the opposite wall. Thus the tubular member 12 is held rigidly in the clamp without slipping and without leaking. The needle 30 extends at an acute angle to the axis of the tube which together with the angle on the tip 32 of the needle avoids cutting plugs in the wall of the tube. Material displaced during the piercing of the tubular member around the needle 30 produces a seal and thus simplifies the injection site. The clamp device can be molded in FDA approved polypropylene. The needle 30 can be of the type commercially available and is molded in place during the molding of the clamp. The extension 48 allows finger control and release, and abrasive portion 38 is added insurance against accidental yanking of the tubing. The cradle formed by the lands 28 provides for proper cradling of the tubing in the needle slot and the device is simple and inexpensive to mold so that it may be disposable after a single use if desired.

Turning now to the device as shown in the embodiments of FIGS. 6–9 of the drawings, there is shown a molded plastic clamp and piercing device 50 for clamping onto and piercing the wall of a tubular member 52. In this embodiment the parts are arranged for industrial application and a clamp of this type has been recently used to tap into and clamp onto tubular conduits transporting maple sucrose. Two clamp jaws 54 and 56 are hingedly connected together by a hinge pin 58 at one end thereof. They are molded with semi-circular depressions 60 and 62 to provide a cradle for the tubular conduit 52 to be pierced. The top jaw 54 is of a softer plastic material than the bottom material 56, for example, the top jaw is of polypropylene with long soft fibrous material therein while the bottom jaw is of harder plastic such as Laxan. Both of these materials are very stable under extreme environmental conditions an work together so that there is no material pickup or appreciable wear at the pivot hinge pin 58 or at the locking tabs.

The jaws include a pair of end tabs 64 and 66 which function to lock the clamp together. They have complementary locking rachet teeth 68 and 70. The tab 66 is integrally molded and extremely flexible as seen by the small integral connection 72 and has an outer extension 74 for finger operation to loosen the clamp when the device is clamped. Guiding sides 76 are integral with the lower clamping jaw.

Figure 9:
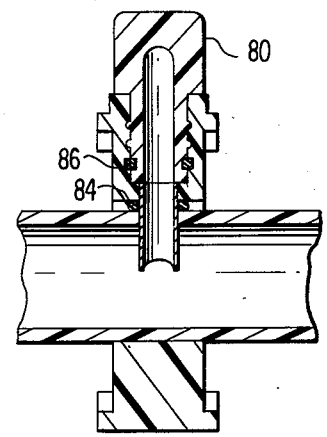
FIG. 9 is a transverse sectional elevation through the clamping device showing the seals and the piercing of the tube.
Figure 8:
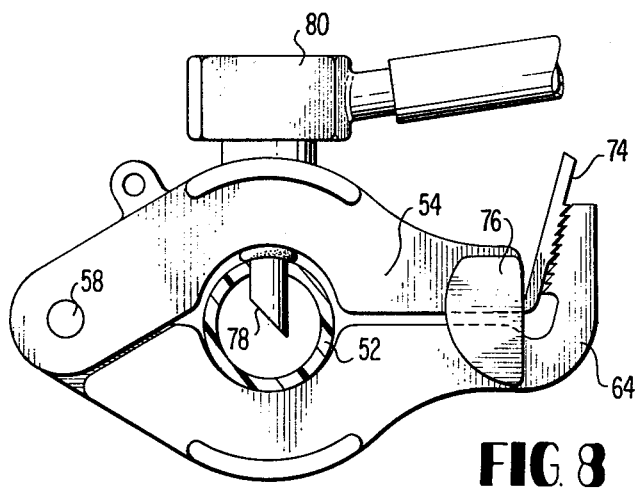
FIG. 8 is an end elevation of the device shown in FIG. 6 with the clamp closed.

The upper clamping 54 bears tubular piercing cutter 76 having an angled hollow point 78 and extending through the top clamp 54 perpendicular to the axis of the tube when the clamp is closed as shown in FIGS. 8 and 9. The tubular cutter 76 is connected to a turnable L-shaped fitting 80 which in turn is connected to a conventional tube 82. For sealing the cutting there is a O-ring seal 84 between the semi-circular depression 60 and around the piercing cutter 76. Ring seal 86 is between the rotatable L-shaped fitting 80 and inside diameter of a raised boss of the upper jaw 54. The fitting 80 being of hard plastic employs molded retaining rings, which when pressed into the soft plastic of upper jaw 54 embeds itself after turning to produce a non-retractable fitting. The soft, fibrous material of the upper jaw 54 allows pivoting at point 72 of the locking tab.

Figure 7:
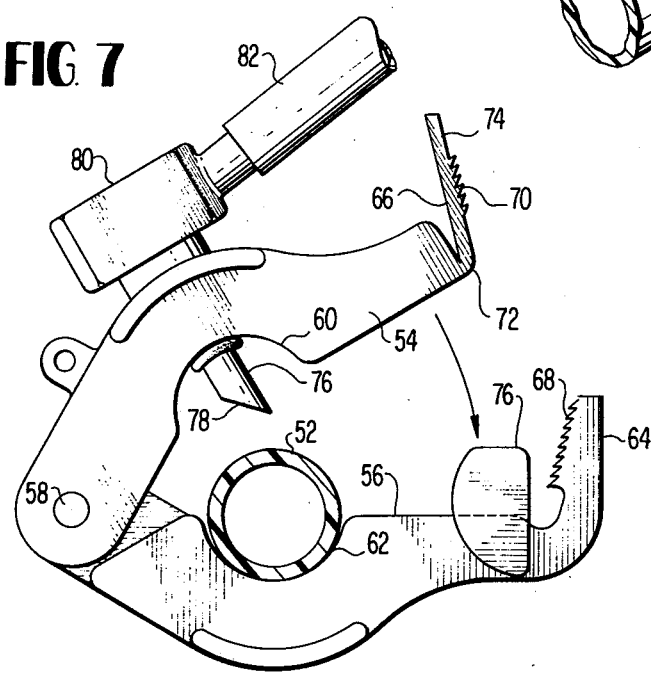
FIG. 7 is an end elevation view of the embodiment shown in FIG. 6 with the clamp opened.

The clamp is inserted on the tube 54 by opening it and after inserting as shown in FIG. 7, the clamp is closed to the position shown in FIG. 8 at which time the piercing cutter 76 will pierce the wall of tube 52 to establish fluid communication and the locking teeth of end tab 66 and 64 will cooperate to hold the device in locking position. The O-ring seals are used to prevent leaks. The clamp can be used to tap a tube within 5 seconds, quickly, easily and inexpensively and in use there are no leaks, flow is visible through transparent fitting 80, and the outlet tube 82 can be rotated to any angle.

Although two specific preferred embodiments have been disclosed, such disclosure is without limitation on the scope of the invention as defined by the appended claims.

What is claimed is:

1. A clamp and piercing device for securely clamping a tubular member and piercing the wall thereof, comprising:

two clamp jaws constituting a clamp body,
a semi-circular depression in each jaw for accommodating a tubular member to be clamped and pierced,
hinge member connecting each clamp jaw at one end thereof to allow opening and closing of the clamp jaws,
a hollow piercing member extending through one of the clamp jaws in the area of the semi-circular depression to thereby pierce a wall of the tubular member held in the clamp when the clamp is closed,
means for attaching a take-off conduit to the hollow piercing member to establish a path for fluid communication with the inside of the tubular member being clamped,
a pair of locking end tabs one at the end of each of the clamp jaws,
means flexibly and integrally connecting one end of at least one end tab to the end of the corresponding clamp jaw,
locking means in the form of locking rachet teeth facing each other on the end tabs arranged so that they can be locked together to secure the clamp jaws in clamping position or unlocked by flexing at least one of the end tabs away from the other to quickly and easily unlock the clamp, and
a finger contact portion on at least the flexibly connected end tab for finger contact for moving such end tab to unlock the rachet teeth locking means.

2. A device as in claim 1 wherein the hinge means is integral with the clamp jaws and the hinge means and the jaws are formed integrally of plastic material.

3. A device as in claim 2 wherein the integrally molded plastic hinge is the wall of a cylindrically molded opening in one end of the clamp jaws.

4. A device as in claim 2 wherein the clamp jaws are molded of plastic and when closed create a cylindrical opening of a size to tightly clamp the tubular member.

5. A device as in claim 2 wherein the hollow piercing tubular member extends at an acute angle to the axis of the tubular member.

6. A device as in claim 5 wherein the end of the hollow piercing member when the jaws are closed is parallel to the axis of the tubular member.

7. A device as in claim 2 further comprising friction creating ring means carried by the clamp jaws in the semi-circular depressions to provide further frictional force clamping the tubular member against longitudinal movement relative to the clamp jaws.

8. A device as in claim 1 wherein the hinge means is a hinge pivot pin extending through one end of the clamp jaws.

9. A device as in claim 8 wherein the hollow piercing member is a piercing cutter tube extending at right angles to the axis of the tubular member and extending through one of the clamp jaws.

10. A device as in claim 8 wherein the clamp jaw carring the piercing cutter is of a softer plastic material than the other clamp jaw and carries the flexible locking tab where the other clamp jaw carries a rigid locking tab.

* * * * *